(12) United States Patent
Gradel

(10) Patent No.: US 8,764,843 B2
(45) Date of Patent: Jul. 1, 2014

(54) COTYLE COMPRISING A STERILE INTERFACE

(76) Inventor: Thomas Gradel, Marignier (FR)

(*) Notice: Subject to any disclaimer, the term of this patent is extended or adjusted under 35 U.S.C. 154(b) by 871 days.

(21) Appl. No.: 12/522,162

(22) PCT Filed: Jan. 8, 2008

(86) PCT No.: PCT/IB2008/050047
§ 371 (c)(1),
(2), (4) Date: Oct. 15, 2009

(87) PCT Pub. No.: WO2008/135868
PCT Pub. Date: Nov. 13, 2008

(65) Prior Publication Data
US 2010/0063597 A1    Mar. 11, 2010

(30) Foreign Application Priority Data
Jan. 8, 2007  (FR) ...................................... 07 52558

(51) Int. Cl.
*A61F 2/34*    (2006.01)
(52) U.S. Cl.
USPC ................... 623/22.12; 623/22.21; 623/22.24
(58) Field of Classification Search
USPC .......... 623/19.12, 19.13, 20.22, 21.13, 21.16, 623/21.17, 22.11, 22.15, 22.16, 22.17, 623/22.18, 22.21, 22.22, 22.23, 22.24, 623/22.25, 22.26, 22.27, 22.28, 22.3, 22.31, 623/22.35, 22.4, 23.39, 23.4, 23.43, 22.12; 606/91, 99
See application file for complete search history.

(56) References Cited

U.S. PATENT DOCUMENTS

| | | | | |
|---|---|---|---|---|
| 3,698,017 A | * | 10/1972 | Scales et al. | 623/22.24 |
| 4,715,860 A | * | 12/1987 | Amstutz et al. | 623/22.33 |
| 5,571,200 A | * | 11/1996 | Cohen et al. | 623/22.12 |
| 5,702,477 A | * | 12/1997 | Capello et al. | 623/22.21 |
| 6,022,357 A | | 2/2000 | Reu | |
| 6,132,469 A | * | 10/2000 | Schroeder | 623/22.24 |
| 2003/0050705 A1 | * | 3/2003 | Cueille et al. | 623/22.24 |
| 2005/0228394 A1 | * | 10/2005 | Bihary et al. | 606/91 |
| 2006/0241781 A1 | * | 10/2006 | Brown et al. | 623/23.43 |

FOREIGN PATENT DOCUMENTS

| | | |
|---|---|---|
| DE | 19640747 A1 | 2/1998 |
| EP | 1188729 A2 | 3/2002 |
| EP | 1290992 A1 | 3/2003 |
| WO | 2004069091 A2 | 8/2004 |

* cited by examiner

*Primary Examiner* — David Isabella
*Assistant Examiner* — Suba Ganesan
(74) *Attorney, Agent, or Firm* — William H. Eilberg

(57) ABSTRACT

A cotyle including a metallic insertion acetabular shell having an outer, essentially hemispherical, convex anchoring face formed in such a way as to be anchored in a cotyloid cavity of the pelvis of a patient, and a concave receiving face. The cotyle also includes a fixed definitive articular ceramic insert having an outer face engaging in the concave receiving face of the metallic insertion acetabular shell, and an inner receiving face including a concave, essentially hemispherical, articular surface for allowing the engagement and pivoting of a femoral prosthesis head or a mobile articular insert. The cotyle is packed in its assembled sterile state, with the definitive fixed articular ceramic insert engaged in the metallic insertion acetabular shell having a peripheral receiving structure that can receive means for fixing an impacter for positioning a cotyle and is designed in such a way that the impacter can be fixed to the cotyle in the presence of the definitive fixed articular ceramic insert.

14 Claims, 10 Drawing Sheets

COTYLE COMPRISING A STERILE INTERFACE

TECHNICAL FIELD OF THE INVENTION

The present invention concerns a prosthetic cotyle intended to replace the natural cotyle of the hip.

A total hip prosthesis comprises two parts constituting a ball joint, namely a female part intended to replace the natural cotyle of the hip and a male part intended to replace the head of the femur.

The male part of the joint generally includes a rod, intended to penetrate into the medullary canal of the femur, and the proximal end of which is connected by a neck to a spherical head intended to penetrate into the cotyle.

The female part of the joint, which must replace the natural cotyle of the hip, and that is referred to overall as the cotyle, usually comprises a hemispherical insertion shell, which is accommodated in a prepared cotyle cavity in the bone of the pelvis, and in which is accommodated a final joint insert. The insertion shell is routinely of metal.

The joint insert is made of a material with a low coefficient of friction such as polyethylene or a ceramic.

In single-motion cotyles, the polyethylene or ceramic insert is fixed into the insertion shell and includes a coaxial and substantially hemispherical joint cavity in which it engages and pivots the spherical head of the male part of the joint. Rotational movements of the joint then occur between the spherical head of the male prosthesis part and the joint cavity of the insert.

When placing the insertion shell in the cotyle cavity, it must be possible to use an impacter to hold and manipulate the insertion shell and to apply to it a force for driving it into the cotyle cavity of the bone with a good orientation, for a period sufficient in particular for a cement to set between the external surface of the insertion shell and the cotyle cavity of the bone.

In single-motion cotyles, the impacter generally includes a threaded end section that is fixed into a threaded hole provided at the center of the insertion shell.

The main problem when using a hip prosthesis is the risk of luxation, i.e. escape of the spherical femoral head from the joint cavity.

To reduce the risks of luxation, double-motion cotyle structures have been proposed in which the insertion shell is of metal and receives a polyethylene joint insert that is itself rotatably mounted in the insertion shell. A drawback of this structure is the occurrence of progressive wear of the joint insert, which causes instability of the joint and a risk of luxation after a few years of use.

Another effective means for preventing luxation is to use, in a single-motion cotyle, a spherical prosthetic femoral head of large diameter. For the spherical femoral head to escape from the joint cavity, the femoral head must come out a distance substantially equal to the radius of the femoral head. Accordingly, the greater the diameter of the prosthetic femoral head, the greater the force necessary for luxation of the prosthesis to occur.

The cotyle cavity of a patient has fixed dimensions, however, which can only be modified with great difficulty (or not at all). The necessary thickness of the fixed joint insert then determines the possible diameter of the prosthetic femoral head. Using a thin fixed joint insert to enable the diameter of the prosthetic femoral head to be increased has therefore been envisaged. To reduce further the thickness of the fixed joint insert to the benefit of the diameter of the femoral head, at the same time as reducing the risks of wear, inserts with a metal insertion shell and ceramic inserts have been envisaged, ceramic having both good low friction properties and greater mechanical strength than polyethylene. The greater mechanical strength of ceramic enables it to withstand the mechanical stresses in the joint even though it is thin. With modern ceramics, fixed joint inserts can be used approximately 4 mm thick or less. One such ceramic insert cotyle is described in the document EP 1 290 992 A1.

To increase further the diameter of the prosthetic femoral head, the above document teaches reducing the thickness of the insertion shell with the same thickness of the ceramic fixed insert. Thus the metal shell has a thickness between 0.1 and 2 mm and the ceramic insert has a thickness less than 4 mm.

However, a great increase in the risks of rupture of the ceramic insert is then observed, either during the impaction of the cotyle to place it, or even during subsequent use of the prosthesis.

According to the present invention, it is considered that such ruptures are caused by an uneven distribution of the mechanical forces on the ceramic insert, noting that the document EP 1 290 992 A1 does not refer to these problems and describes no means for correct impaction of the cotyle.

STATEMENT OF THE INVENTION

The problem addressed by the present invention is reducing the risk of luxation of a hip prosthesis at the same time as reducing the risks of rupture of the ceramic insert as much during its impaction into the cotyle cavity of the pelvis of a patient as during subsequent use of the prosthesis.

To achieve the above and other objects, the invention proposes a cotyle comprising:

a metal insertion shell, having a substantially hemispherical convex exterior anchor face conformed to be anchored in a cotyle cavity in the pelvis of a patient, and having a concave receiving face with an annular edge, a ceramic fixed final joint insert, having an exterior face engaged in the concave receiving face of the insertion shell, and having an interior receiving face including a substantially hemispherical concave joint surface to enable the engagement and the pivoting of a femoral prosthesis head or of a mobile joint insert, the ceramic fixed final joint insert having a thickness less than or equal to approximately 4 mm, the insertion shell comprising an annular receiving structure projecting beyond the receiving face of the fixed final joint insert inserted in the insertion shell and including an annular receiving face conformed so that an impacter can be fixed to said annular receiving face in the presence of the ceramic fixed final joint insert, the insertion shell having, in the vicinity of its annular edge, a thickness less than or equal to approximately 4 mm and greater than 2 mm.

Thanks to the small thickness of the insertion shell and the joint insert, a maximum dimension can be given to the femoral head and to the concave joint surface to reduce effectively the risks of luxation of the joint during subsequent use. At the same time, despite these small thicknesses, the annular receiving structure not only provides effective retention of the cotyle during its impaction by an impacter but also effective cooperation between the insertion shell and the joint insert when assembled prior to impaction. This cooperation reduces the risks of deformation of the insertion shell during impaction because the ceramic joint insert remains in contact with the insertion shell and absorbs some of the forces. This cooperation also reduces the risks of rupture of the joint insert during impaction, the impaction forces being applied to the insertion shell, which thereafter transmits them in a distributed manner over the ceramic joint insert. After impaction, this cooperation also reduces the risks of subsequent rupture of the joint insert, because the mechanical forces are transmitted in a regular and distributed manner between the joint insert and the insertion shell which has not been deformed.

During placement, the insertion shell remains attached to the fixed final joint insert. The interface between these two parts therefore remains inaccessible and sterile, with no risk of contamination during the operation.

Because the peripheral receiving structure projects beyond the receiving face of the fixed final joint insert inserted into the insertion shell, and thanks to the sufficient thickness of the insertion shell in the vicinity of its annular edge, i.e. in the area constituting the peripheral receiving structure, reliable fixing of the impacter to the insertion shell is possible, despite the presence of the fixed final joint insert preventing access to any threaded hole provided at the center of the insertion shell.

Moreover, in the extreme positions of use of the prosthesis, the prosthetic neck carrying the prosthetic femoral head comes to bear against the projecting peripheral receiving structure. Thus the prosthetic neck does not abut against the fixed final ceramic insert and there is therefore no risk of it being damaged by the application of a localized point load.

The annular receiving face preferably extends from and is continuous with the concave receiving face of the insertion shell and is therefore an annular portion of the interior face of the insertion shell. Such a peripheral receiving structure is compact and easy to produce using ordinary production means. This peripheral receiving structure is also in one piece with the insertion shell and is therefore reliable to enable the surgeon to apply the necessary forces for good fixing and good orientation of the prosthesis.

The cotyle can advantageously be associated with a placement and orientation insert, removably fixed to the peripheral receiving structure of the insertion shell, and including an assembly structure to which the impacter can be removably fixed. This kind of insert, fixed to the periphery of the insertion shell, achieves a good distribution over the shell of the forces applied by the surgeon to fix and orient the prosthesis.

According to another advantageous aspect of the invention, the cotyle is packaged assembled in the sterile state, with the ceramic fixed final joint insert engaged in the insertion shell and with the placement and orientation insert fixed to the insertion shell.

One benefit of such a combination is that the placement and orientation insert retains the ceramic joint insert in the insertion shell during transportation and manipulation. It is thus possible to provide a joint insert that is simply engaged in the insertion shell, and which can then be extracted therefrom if the surgeon requires, without there being any risk of accidental extraction before the placement of the cotyle. This combination can be used independently of the thickness characteristics of the joint insert and the insertion shell.

To strengthen further the joint insert, the placement and orientation insert fixed to the annular receiving face of the insertion shell can bear on or be at a small distance from the interior receiving face of the ceramic fixed final joint insert.

Alternatively or in addition to this, the placement and orientation insert, fixed to the annular receiving face, can include one or more projecting elastic ribs adapted to come to bear on the ceramic fixed final joint insert to retain it in the insertion shell.

The placement and orientation insert can be of polyethylene, a low-cost material that can easily be sterilized and can be used in the surgical environment.

The assembly structure can preferably comprise a threaded fixing hole formed in the placement and orientation insert, enabling the screwing in of a corresponding threaded portion of the impacter. This produces a simple, reliable and inexpensive assembly structure allowing the use of known and available impacters.

According to a first advantageous embodiment of the invention:
the peripheral receiving structure can include a continuous or discontinuous annular groove,
the placement and orientation insert can include a continuous or discontinuous annular rib elastically engaged in the annular groove.

According to a second advantageous embodiment of the invention:
the peripheral receiving structure can include an internal or external thread,
the placement and orientation insert can include an external or internal thread, cooperating with the thread of the peripheral receiving structure to fix the placement and orientation insert removably by screwing it to the peripheral receiving structure.

The various peripheral receiving structures and the placement and orientation insert are therefore easy and inexpensive to produce and provide sufficient strength for the surgeon to be able to apply the necessary forces for good fixing and good orientation of the prosthesis.

In the first embodiment of the invention, the threaded fixing hole can advantageously be an open hole, adapted to cooperate with a detachment tool including a threaded rod adapted to be screwed into the fixing hole and that has a distal end conformed to bear against the concave joint surface of the fixed final joint insert during screwing of the threaded rod into the fixing hole of the placement and orientation insert.

Alternatively, in the first embodiment of the invention, it can advantageously be provided that:
the placement and orientation insert can be conformed so that there remains a free space between the placement and orientation insert and the bottom of the concave joint surface of the fixed final joint insert once the placement and orientation insert is fixed to the peripheral receiving structure of the insertion shell,
the placement and orientation insert can be in sealed contact at its periphery in the short annular extension of the insertion shell,
the fixing hole can be an open hole, providing communication between the exterior and the free space between the placement and orientation insert and the fixed final joint insert, and sized to engage therein in a sealed manner the end of a syringe.

Another aspect of the invention proposes a method of producing a prosthetic hip cotyle, comprising the steps of:
a) providing a metal insertion shell having a concave receiving face and a projecting annular receiving structure,
b) providing a ceramic joint insert having an exterior face and a concave joint surface,
c) engaging the exterior face of the joint insert in the concave receiving face of the insertion shell,
d) sterilizing the combination thus formed in a microbial protection envelope.

The benefit is both to make the prosthesis more sterile, notably at the interface between the joint insert and the insertion shell, at the same time as enabling the use of a joint insert simply engaged removably in the insertion shell.

Sterilization can be effected after assembly of the joint insert and the insertion shell, by bombardment with gamma rays. This kind of sterilization process is compatible with the materials used, namely the metal of the insertion shell and the ceramic of the joint insert.

The method can advantageously further comprise, before sterilization, the additional step c1) of fixing to the insertion shell a placement and orientation insert.

This method, with or without the step of fixing the placement and orientation insert, can be used independently of the presence or absence of the particular thickness characteristics of the joint insert and the insertion shell.

Another aspect of the invention further proposes such a method including the subsequent steps of:
  e) opening the sealed envelope in the operating room,
  f) fixing an impacter to the cotyle,
  g) engaging the cotyle in the cotyle cavity in the bone and impacting the cotyle to fix it to the bone.

BRIEF DESCRIPTION OF THE DRAWINGS

Other objects, features and advantages of the present invention will emerge from the following description of particular embodiments, given with reference to the appended figures, in which.

DESCRIPTION OF THE PREFERRED EMBODIMENTS

Figure 1:
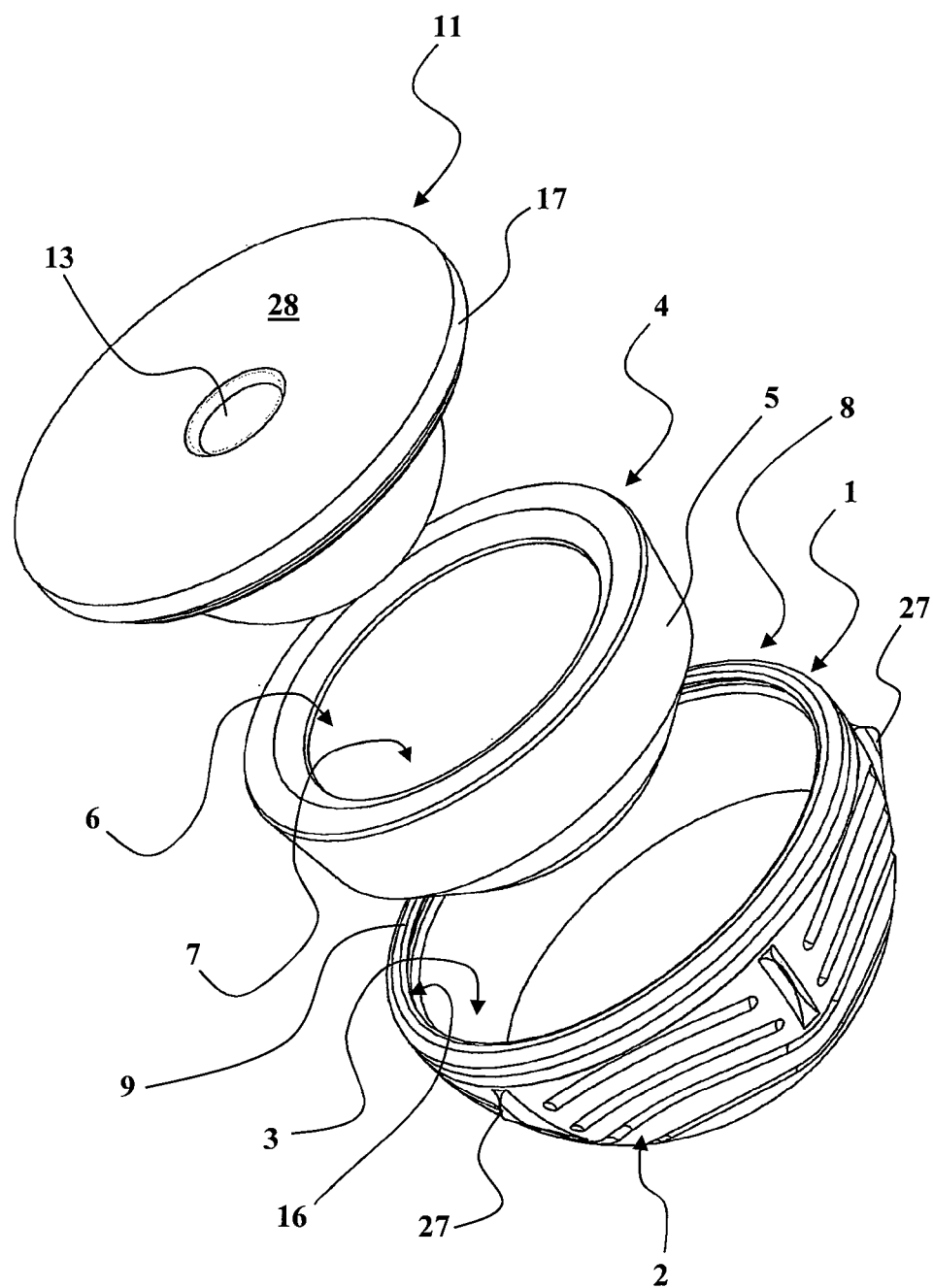
FIG. 1 is an exploded view of a cotyle of the invention with a placement and orientation insert.
Figure 3:
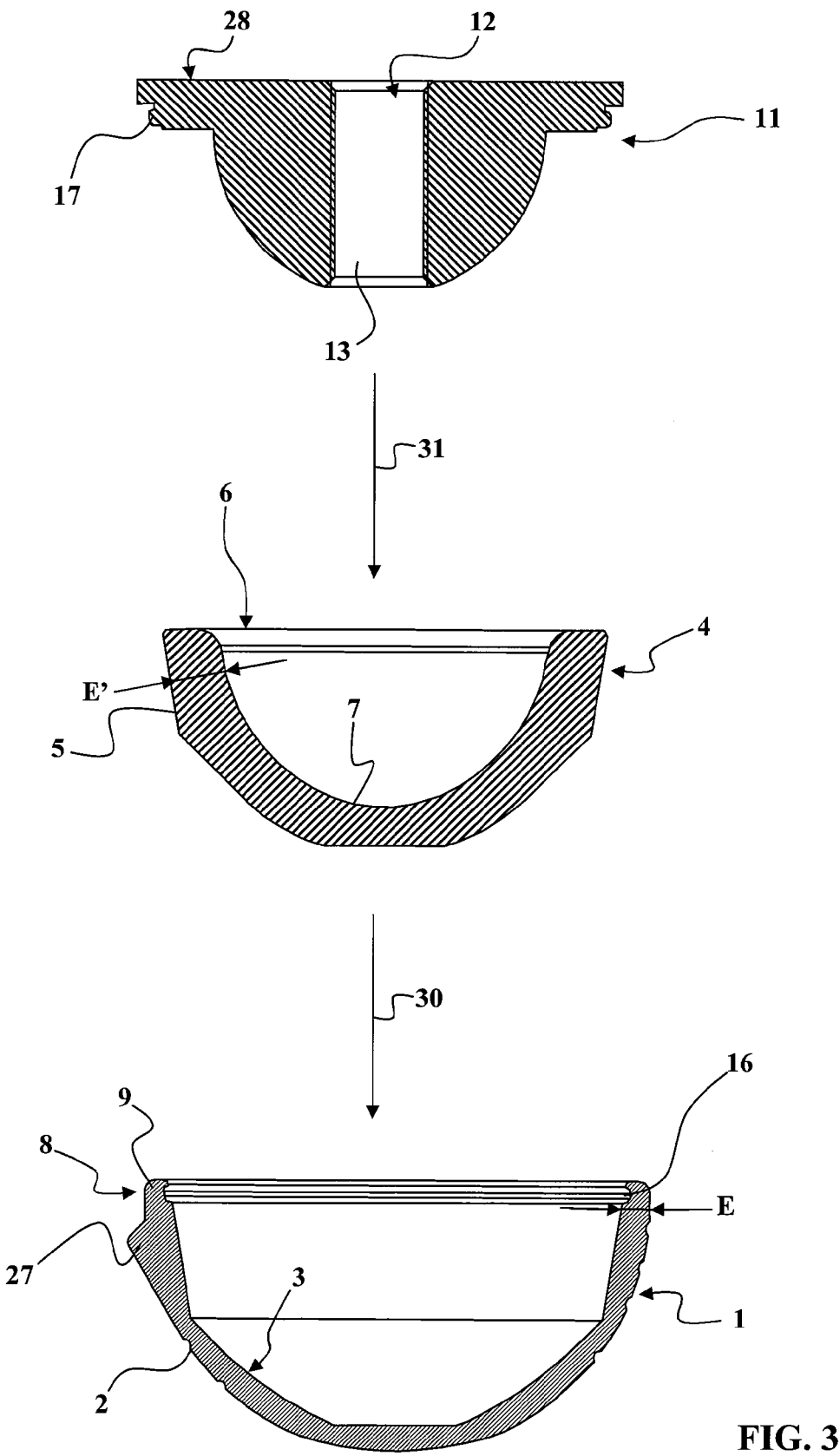
FIG. 3 is a sectional view of the elements from FIG. 1.
Figure 4:
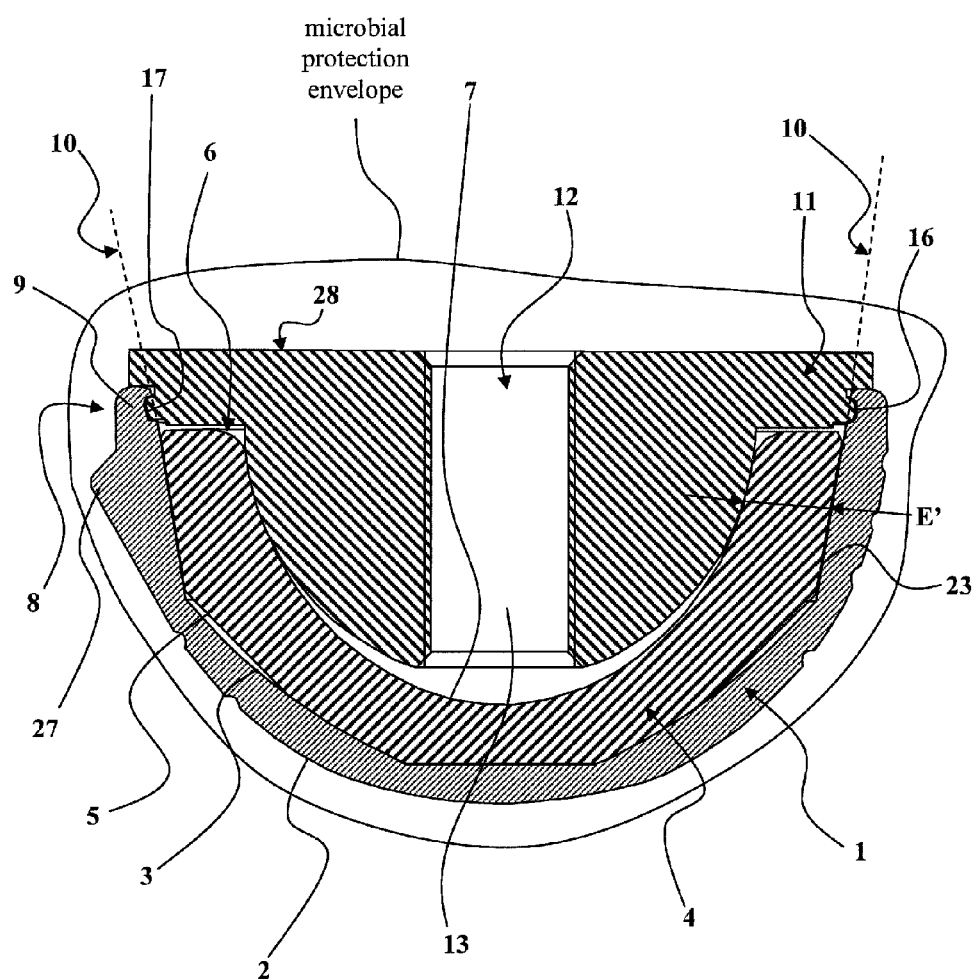
FIG. 4 is a sectional view of the elements from FIG. 1 after assembly.

In FIGS. 1, 3 and 4 there is represented a single-motion or double-motion cotyle. The latter comprises:
  an insertion shell 1, having a substantially hemispherical convex exterior anchoring face 2 conformed to be anchored in a cotyle cavity in the pelvis of a patient, and having a concave receiving face 3,
  a ceramic fixed final joint insert 4, having an exterior face 5 that engages in the concave receiving face 3 of the insertion shell 1, and having an interior receiving face 6 including a substantially hemispherical concave joint surface 7 to enable engagement and pivoting of a femoral prosthesis head or a mobile joint insert (not represented).

The final joint insert 4 is called the fixed final joint insert because it is fixed relative to the insertion shell 1.

In FIGS. 1, 3 and 4, the insertion shell 1 includes anchoring fins 27 intended to penetrate into the bone of the cotyle cavity of the patient to assure good anchoring of the insertion shell 1.

FIGS. 1 and 3 are exploded views respectively in perspective and in section, and FIG. 4 is a view in section of the elements from FIGS. 1 and 3 when assembled together.

In the FIG. 4 configuration, the cotyle is packaged in the sterile state assembled to the ceramic fixed final joint insert 4 engaged in the insertion shell 1. The insertion shell 1 comprises a peripheral receiving structure 8 adapted to receive means for fixing a cotyle placement impacter and shaped so that the impacter can be fixed to the cotyle with the ceramic fixed final joint insert 4 engaged in the insertion shell 1.

The ceramic fixed final joint insert 4 has a small thickness E' to enable the use of a prosthetic femoral head of large diameter.

To characterize the thickness of a joint insert, its mean thickness in different directions perpendicular to its concave joint surface is generally considered. When a joint insert has a flat bottom, as in the fixed final joint insert 4 of FIGS. 1, 3 and 4, the thickness of that bottom is generally not taken into account to determine its mean thickness.

The thickness of the fixed final joint insert 4 is therefore substantially equal to the thickness E' represented in FIGS. 3, 4 and 6 to 8.

To reduce the risk of luxation effectively, a small thickness E' is chosen to increase the diameter of the prosthetic femoral head (not represented) intended to be inserted into the concave joint surface 7 of the fixed final joint insert 4 (in the case of a single-motion cotyle of the type described in the document EP 1 290 992 A1) or to enable the use of a mobile joint insert (not represented) intended to receive the prosthetic femoral head (as in the case of a double-motion cotyle of the type described in the document WO 2004/069091).

The thickness E' is chosen so that the fixed final joint insert 4 can withstand the stresses produced during normal use of the hip prosthesis by a patient without premature wear or deterioration.

By a small thickness E' is meant a thickness E' less than or equal to approximately 4 mm, preferably less than or equal to 3.5 mm. A ceramic such as that described in the document EP 1 188 729 can be used for this purpose, among others.

To characterize the thickness of an insertion shell, its thickness in the vicinity of the upper edge of its concave receiving face is generally considered. The thickness of the insertion shell 1 is therefore substantially equal to the thickness E represented in FIGS. 3 and 6 to 9. This thickness E is the mean thickness of the insertion shell 1 in the vicinity of the annular edge 9 of the concave receiving face 3 of the insertion shell 1.

To reduce further and effectively the risk of luxation for a single-motion or double-motion cotyle, a small thickness E is chosen. By a small thickness E is meant a thickness E less than or equal to approximately 4 mm, preferably less than or equal to 3 mm, but greater than 2 mm to guarantee sufficient mechanical strength.

Figure 8:
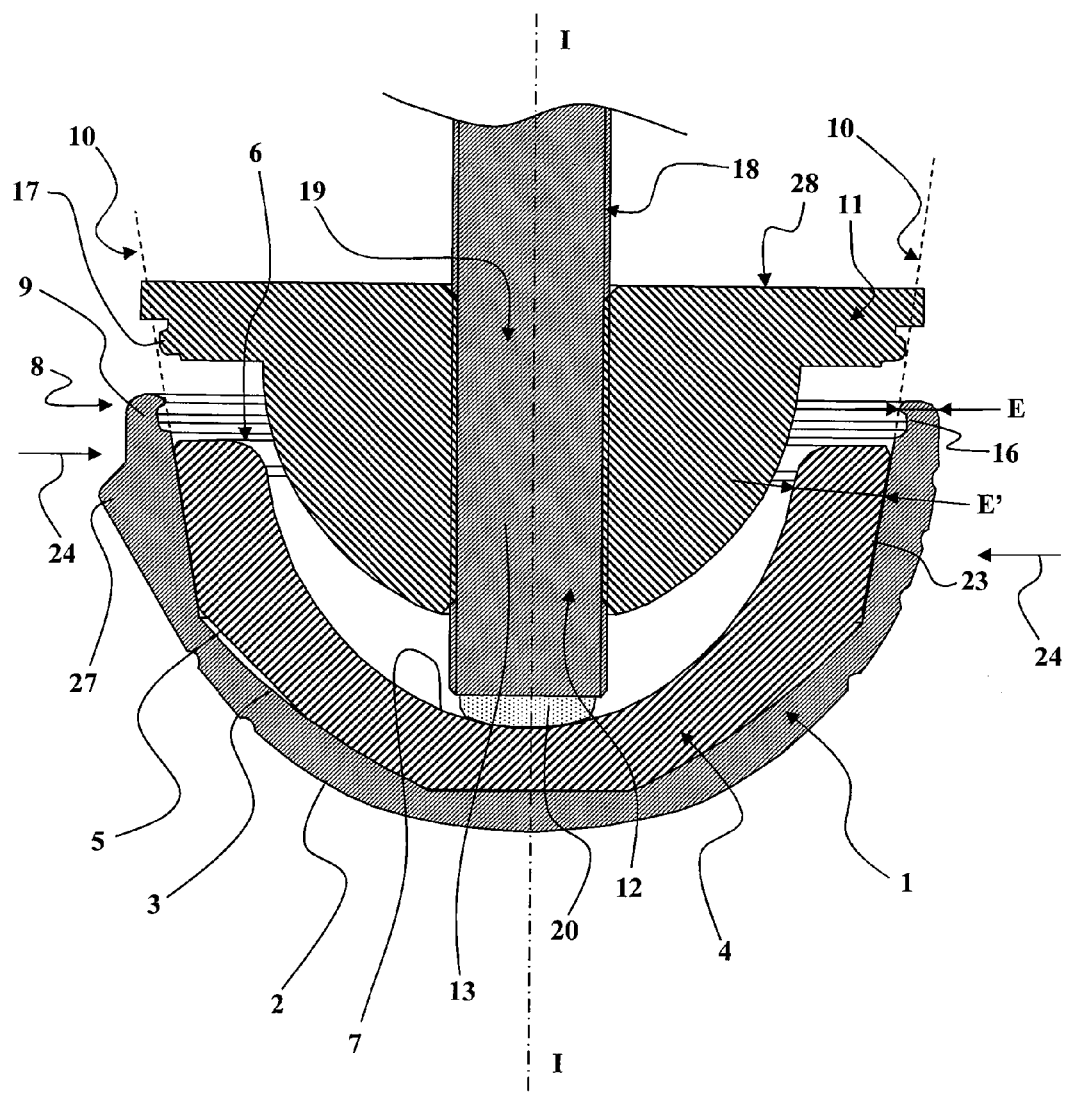

It is seen more particularly in FIGS. 4 and 8 that the insertion shell 1 includes a peripheral receiving structure 8 that projects beyond the receiving face 6 of the fixed final joint insert 4 inserted into the insertion shell 1.

The peripheral receiving structure 8 constitutes a short annular extension of the wall of the insertion shell 1, with, in this embodiment, an interior annular receiving face 10 (shown in dashed line in FIGS. 4 and 8) extending from and continuous with the concave receiving face 3 of the insertion shell 1.

In the embodiments of FIGS. 1 to 9, to enable the fixing of an impacter, a placement and orientation insert 11 is provided, removably fixed to the peripheral receiving structure 8 of the insertion shell 1. The placement and orientation insert 11 can thus be fastened to the insertion shell 1 in the presence of the ceramic fixed final joint insert 4 engaged in the insertion shell 1 (FIGS. 4, 5, 6, 7 and 9), and can be separated from the insertion shell 1 (as shown better in FIG. 8) after impaction of the cotyle into the cotyle cavity of the patient.

The placement and orientation insert 11 includes an assembly structure 12 to which an impacter can be removably fixed.

The placement and orientation insert 11, once fixed to the periphery to the insertion shell 1, distributes over the insertion shell 1 the forces applied by the surgeon to fix and orient the prosthesis by means of an impacter.

Figure 5:
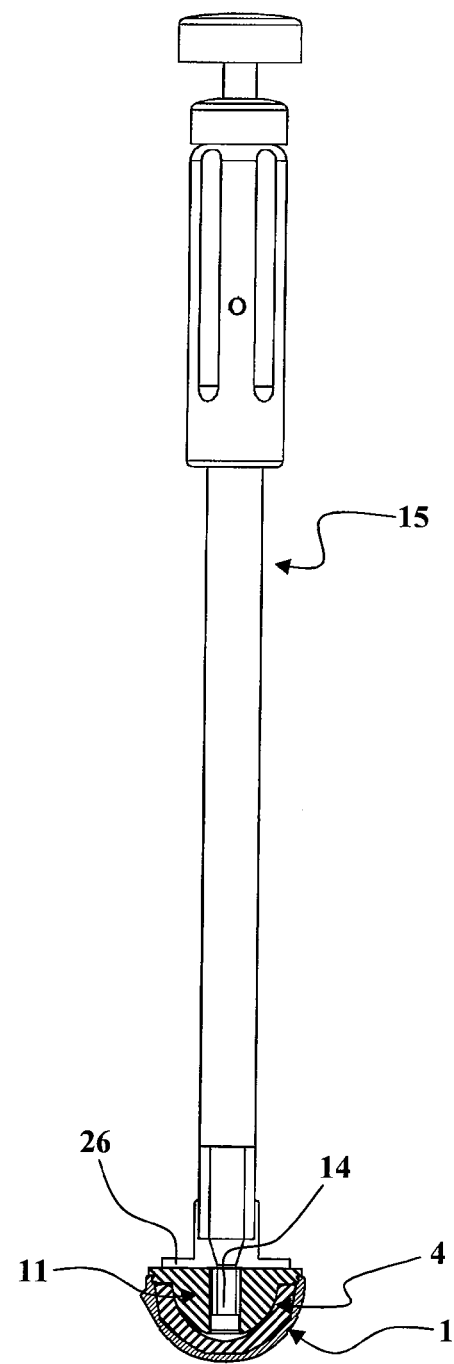
FIG. 5 is a part-sectional view of a cotyle of the invention fixed to an impacter.
Figure 6:
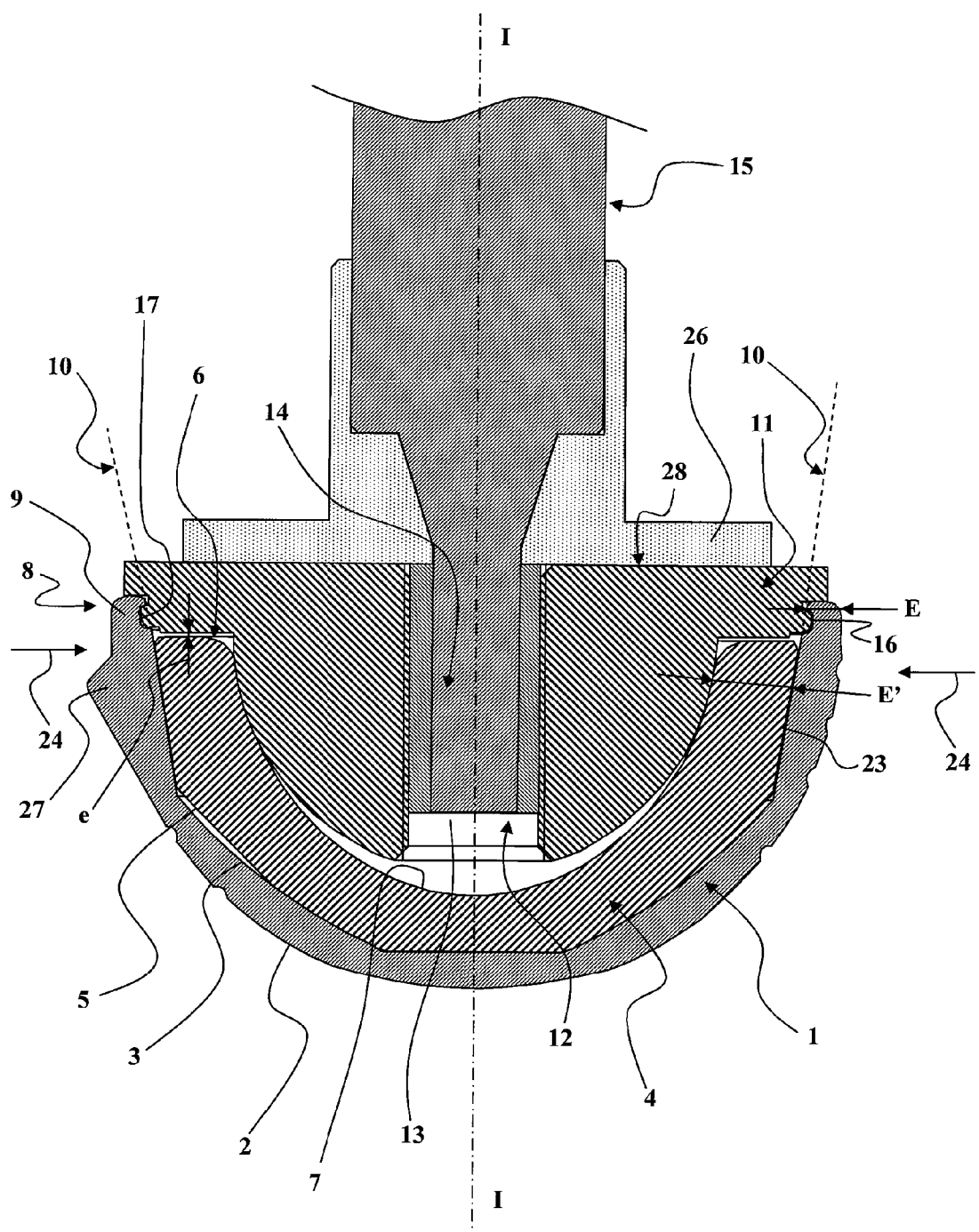
FIG. 6 is a view of a detail from FIG. 5.

In the embodiment represented in FIGS. 1 to 9, the assembly structure 12 includes a threaded fixing hole 13 produced in the placement and orientation insert 11. This threaded fixing hole 13 has a threaded portion 14 of the impacter 15 screwed into it (FIGS. 5 and 6). Accordingly, to detach the impacter 15 from the placement and orientation insert 11, it suffices to unscrew the threaded portion 14 of the impacter 15 from the threaded fixing hole 13.

In the embodiment shown in FIGS. 1 to 9, the peripheral receiving structure 8 includes an annular groove 16 in which is engaged an annular rib 17 provided on the placement and orientation insert 11. The annular rib 17 is elastically engaged in the annular groove 16 when assembling the insertion shell 1, the fixed final joint insert 4 and the placement and orientation insert 11, which assembly process is shown diagrammatically in FIG. 3 by the arrows 30 and 31.

In the embodiment shown in FIGS. 1 to 9, the annular groove 16 and the annular rib 17 are continuous. The continuous character of the annular groove 16 and the annular rib 17 enables homogeneous and maximum retention of the placement and orientation insert 11 in the insertion shell 1 around its entire periphery.

However, other forms of annular rib 17 and annular groove 16 can be envisaged. For example, the annular groove 16 and the annular rib 17 can be discontinuous.

Similarly, the respective dispositions of the annular groove 16 and the annular rib 17 on the placement and orientation insert 11 or the insertion shell 1 can be different from those represented in FIGS. 1 to 9.

In FIGS. 1 to 9, the annular groove 16 is provided on the annular interior receiving face 10 of the peripheral receiving structure 8 of the insertion shell 1 while the annular rib 17 of the placement and orientation insert 11 is an exterior annular rib 17, elastically engaged in the annular groove 16. The placement and orientation insert 11 does not project laterally beyond the periphery of the insertion shell 1. There is therefore no risk of conflict, during impaction and orientation of the cotyle, between the placement and orientation insert 11 and the bony material of the pelvis of the patient at the periphery of their cotyle cavity.

In another embodiment of the invention not shown in FIGS. 1 to 9, the peripheral receiving structure 8 and the placement and orientation insert 11 include threads that cooperate with each other to fix the placement and orientation insert 11 removably by screwing it onto the peripheral receiving structure 8. The thread of the peripheral receiving structure 8 is an internal thread when the thread of the placement and orientation insert 11 is an external thread, and the thread of the peripheral receiving structure 8 is external when the thread of the placement and orientation insert 11 is an internal thread.

At the time of use, the cotyle is packaged assembled in the sterile state, with the ceramic fixed final joint insert 4 engaged in its insertion shell 1 (FIG. 4). To place the insertion shell 1 in the cotyle cavity, the surgeon uses an impacter 15 with a threaded end section 14 that is fixed into the threaded fixing hole 13 produced in the placement and orientation insert 11 (FIGS. 5 and 6).

The impacter 15 includes a flange 26 bearing against the upper face 28 of the placement and orientation insert 11. The flange 26 distributes the impaction and orientation forces on the placement and orientation insert 11.

The surgeon uses the impacter 15 to apply a force for driving the insertion shell 1 into the cotyle cavity of the bone, to apply rotation torques to adjust the orientation of the insertion shell 1, and to hold the insertion shell 1 in a fixed position for a period sufficient in particular for a cement between the external surface of the insertion shell 1 and the cotyle cavity in the bone to set.

During these operations, the insertion shell 1 is subjected to high forces which, because of the small thickness E (FIG. 6), could deform the insertion shell 1 alone in contact with the bone of the pelvis of the patient. This deformation of the insertion shell 1 during impaction of the insertion shell 1 is prevented by the presence of the fixed final joint insert 4 engaged in the insertion shell 1.

Accordingly, if the bone of the pelvis of the patient tends to deform the insertion shell 1 because of its small thickness E, the ceramic fixed final joint insert 4 is sufficiently rigid and strong to counter any deformation. The ceramic fixed final joint insert 4 stiffens the insertion shell 1.

The insertion shell 1, the fixed final joint insert 4 and the placement and orientation insert 11 can advantageously be packaged together in the sterile state. The surgeon can then impact the insertion shell 1 with its fixed final joint insert 4 in a single operation. This saves the surgeon precious operating time, which helps to reduce the risks of the operation linked to possible infection.

Once the insertion shell 1 fitted with its fixed final joint insert 4 has been impacted, the surgeon removes the placement and orientation insert 11 from the peripheral receiving structure 8 of the insertion shell 1 and lodges the chosen prosthetic femoral head in the concave joint surface 7 of the fixed final joint insert 4.

Figure 7:
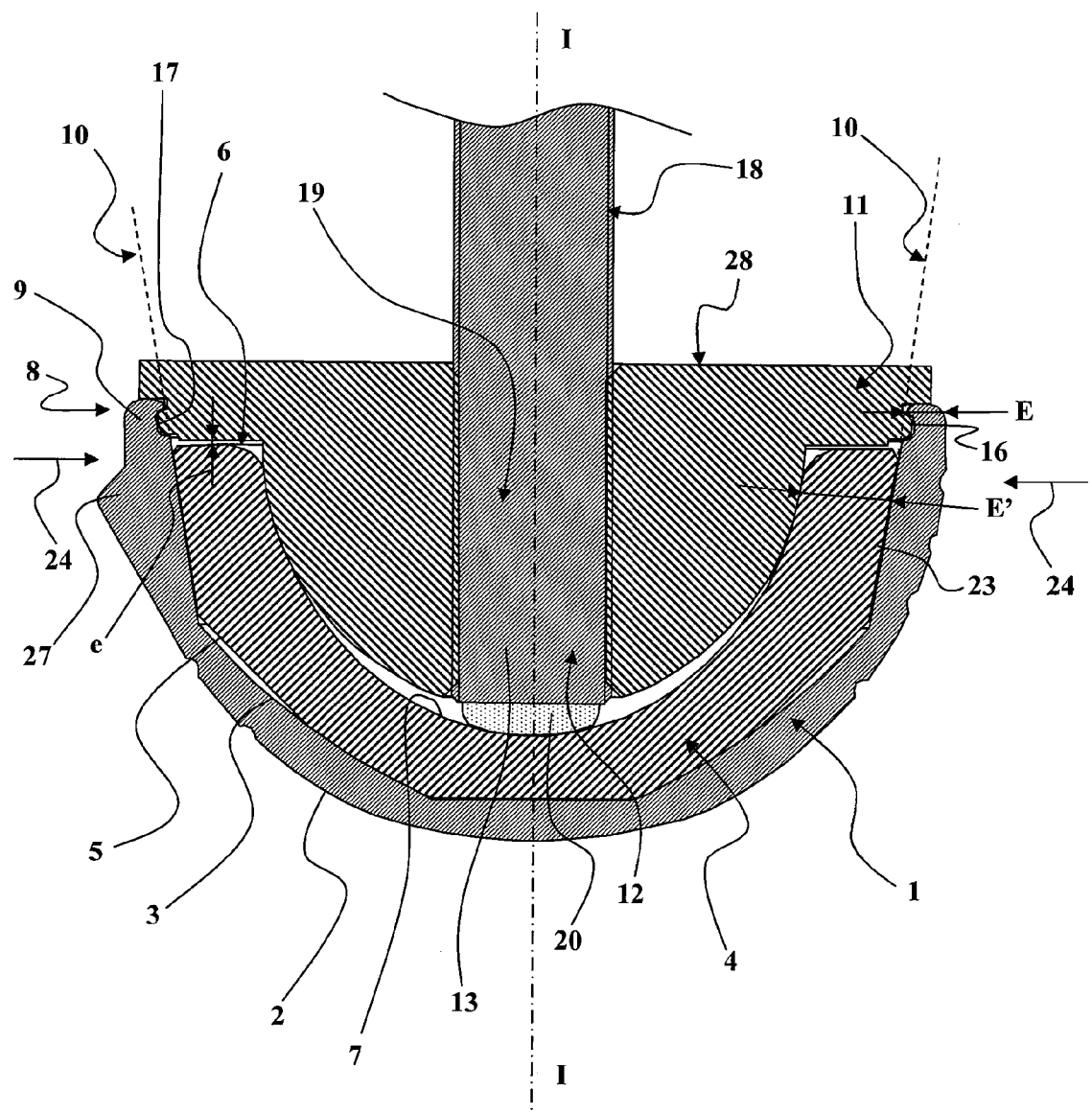
FIGS. 7 and 8 are sectional views illustrating a first way of detaching the placement and orientation insert.
Figure 9:
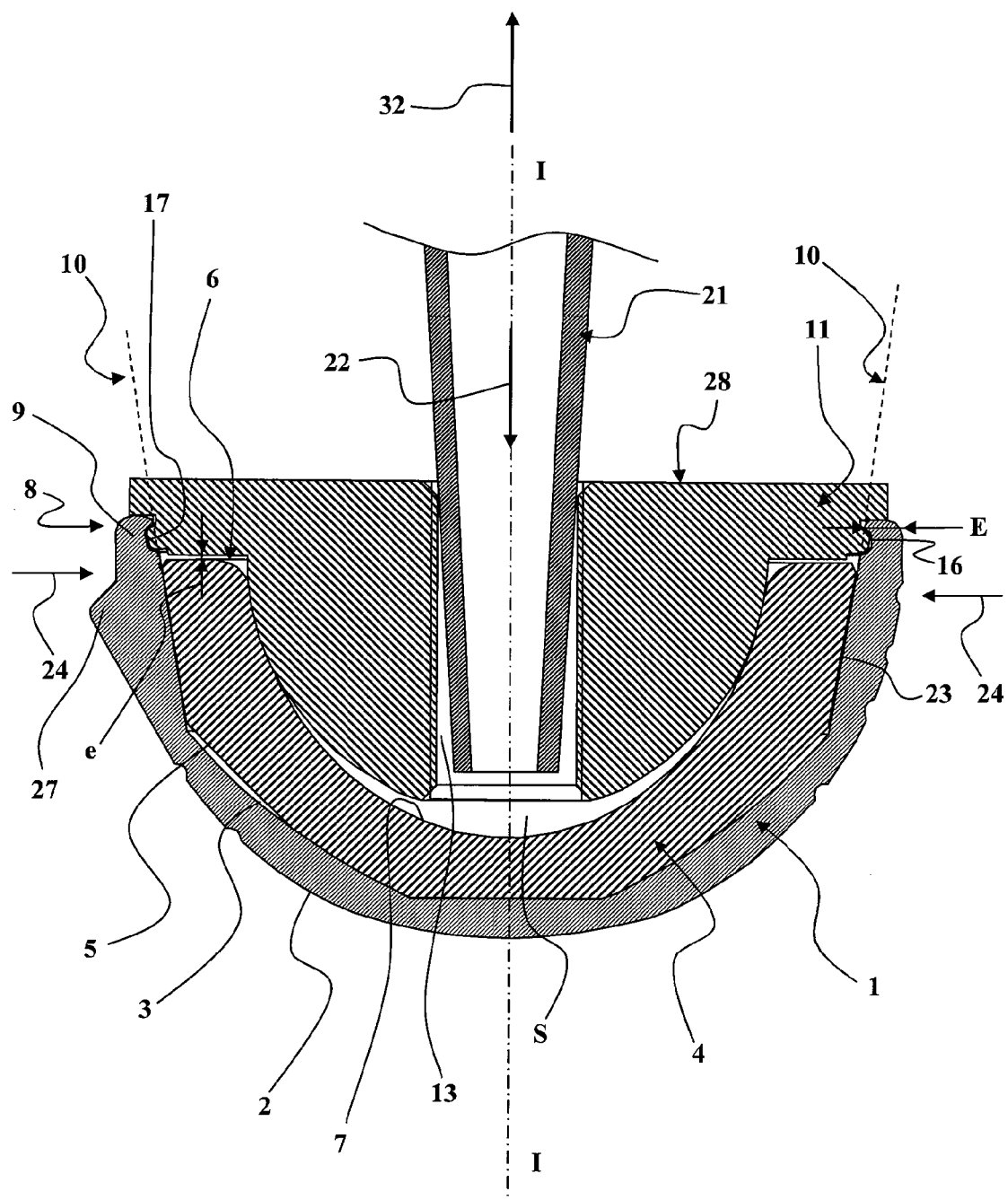
FIG. 9 is a sectional view illustrating a second way of detaching the placement and orientation insert.

The step of detaching the placement and orientation insert 11 from the insertion shell 1 is more particularly represented in FIGS. 7 to 9.

A first way of detaching the placement and orientation insert 11 is shown in FIGS. 7 and 8.

In those FIGS. 7 and 8, the open threaded fixing hole 13 enables engagement of a detachment tool 18 including a threaded rod 19 adapted to be screwed into the fixing hole 13. The detachment tool 18 has a distal end 20 conformed to bear against the concave joint surface 7 of the fixed final joint insert 4 when screwing the threaded rod 19 into the fixing hole 13 of the placement and orientation insert 11.

Screwing the threaded rod 19 into the fixing hole 13 (by turning it one way or the other depending on the configuration of the threads used) moves the placement and orientation insert 11 away from the insertion shell 1 in the axial direction I-I until it is completely detached (FIG. 8) when the annular rib 17 of the placement and orientation insert 11 has escaped elastically from the annular groove 16.

The distal end 20 of the detachment tool 18 is adapted to bear against the concave joint surface 7 of the fixed final joint insert 4 without damaging the latter.

A second way of detaching the placement and orientation insert 11 is shown in FIG. 9.

In this FIG. 9, the placement and orientation insert 11 is conformed so that there remains a free space S between the placement and orientation insert 11 and the bottom of the concave joint surface 7 of the fixed final joint insert 4 once the placement and orientation insert 11 has been fixed to the peripheral receiving structure 8 of the insertion shell 1. The placement and orientation insert 11 is in sealed contact along its periphery in the short annular extension 9 of the insertion shell 1.

The open character of the fixing hole 13 provides communication between the exterior and the free space S formed between the placement and orientation insert 11 and the fixed final joint insert 4.

The fixing hole 13 is sized to enable the engagement of the end of a pressurized fluid feed pipe 21.

The pipe 21 feeds a fluid from the exterior into the free space S as shown by the arrow 22. The fluid then fills the free space S and the fluid pressure in the pipe 21 and in the free space S produces a thrust along the axis I-I on the placement and orientation insert 11 in the direction defined by the arrow 32. With sufficient fluid pressure and a sufficient area of the placement and orientation insert 11 to which that pressure can be applied, the placement and orientation insert 11 is quickly and easily withdrawn from the insertion shell 1 by causing the annular rib 17 to escape from the annular groove 16.

In practice, good results have been obtained using a syringe. The fluid feed pipe 21 can then be the end of a syringe. Using a syringe proves particularly beneficial in the medical context. This is a routine medical object that can be sterilized and is easily usable in an operating room. Alternatively, the fluid feed pipe 21 can be a tubular part of the impacter itself.

The fluid used to detach the insertion shell 1 from the placement and orientation interface 11 can be water or physiological serum, fluids that can be used and are very widely used in operating rooms.

In practice, good results have been obtained using a polyethylene placement and orientation insert 11. Polyethylene is a material that can be used in an operating room, easily sterilized and of low cost.

In FIG. 6, it is seen that the placement and orientation insert 11 is fixed to the peripheral receiving structure 8 of the insertion shell 1 at a small distance e from the interior receiving face 6 of the ceramic fixed final joint insert 4. This distance e enables reliable and secure engagement of the annular rib 17 in the annular groove 16 around the whole of its periphery. Furthermore, during impaction of the cotyle into the cotyle cavity of the pelvis of a patient, the placement and orientation insert 11 will be deformed very slightly by the axial impaction forces along the axis I-I to come to an ever shorter distance from or to bear on the interior receiving face 6 of the ceramic fixed final insert 4 or on its peripheral edge.

If the polyethylene placement and orientation insert 11 comes to bear on the interior receiving face 6 of the ceramic fixed final joint insert 4 or on its peripheral edge, the fixed final joint insert 4 transmits the forces that impact and orient the cotyle. The fixed final joint insert 4 is further held pressed against the concave receiving face 3 of the insertion shell 1, which guarantees that the fixed final joint insert 4 contributes to the stiffness of the insertion shell 1 and prevents any deformation of the latter.

If, during impaction of the cotyle, there remains a large distance e between the placement and orientation insert 11 and the interior receiving face 6 of the ceramic fixed final joint insert 4, as shown in FIGS. 4 and 6 to 9, a conical fit 23 can be provided between the fixed final joint insert 4 and the insertion shell 1. It is then certain, despite the presence of the distance e and the shocks caused by impaction, that the fixed final joint insert 4 contributes to the stiffness of the insertion shell 1 and prevents any deformation of the latter in particular against deformations that can occur because of radial forces, indicated by the arrows 24, induced by the bony material of the pelvis of the patient.

Figure 10:
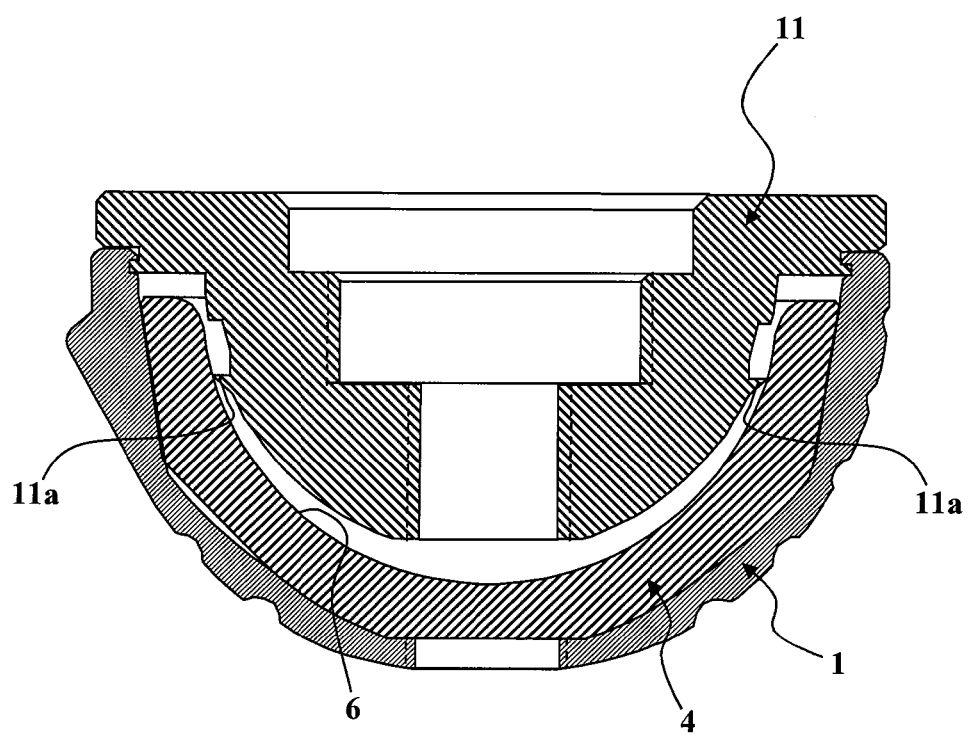
FIG. 10 shows a cotyle the placement and orientation insert whereof further comprises elastic ribs for retaining the joint insert.

In the embodiment shown in FIG. 10, the placement and orientation insert 11 has a projecting elastic rib 11a that comes to bear elastically against the ceramic joint insert 4 in order to hold it pressed into the insertion shell 1. In the embodiment shown, the rib 11a is in the form of an annular lip and comes to bear against the interior receiving face 6. Alternatively, a rib can be provided that comes to bear on the front peripheral edge of the ceramic joint insert 4, or a number of ribs or other elastic shapes can be provided that come to bear simultaneously on the joint insert 4.

Clearly, in contrast to the single-motion cotyles generally known, the presence of the ceramic fixed final joint insert 4 engaged in the insertion shell 1 rules out the use of fixing screws for fixing the insertion shell 1 in the cotyle cavity of the pelvis of the patient through holes through the insertion shell from its concave receiving face to its convex exterior anchor face 2.

Figure 2:
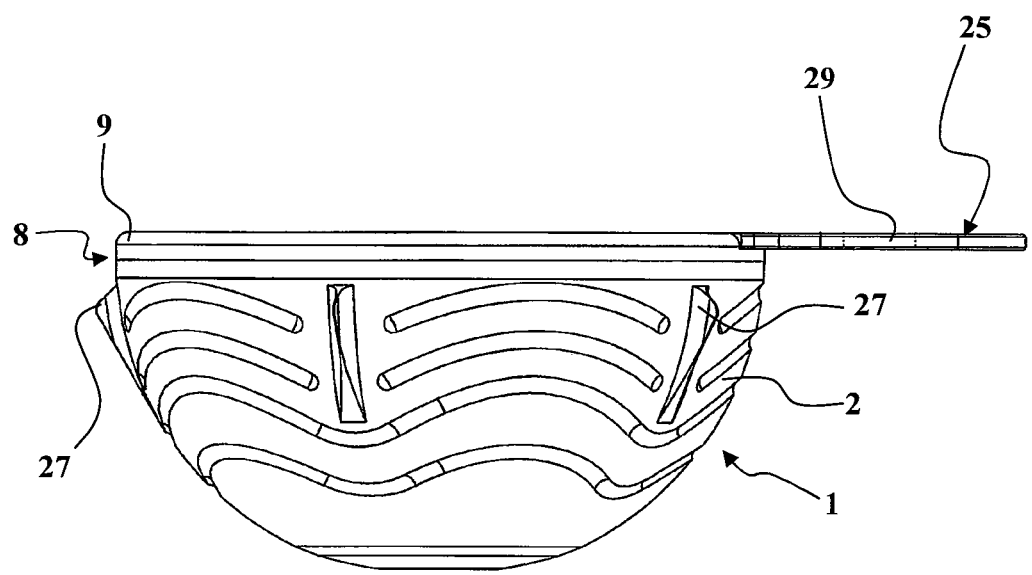
FIG. 2 is a side view of an insertion shell.

In this case, it can be beneficial to provide, in the vicinity of the upper edge of the convex exterior anchor face 2 of the insertion shell 1, an external fixing lug 25 shown in FIG. 2. This external fixing lug 25 includes an opening 29 through which a screw (not shown) passes to be anchored in the bone of the pelvis of the patient.

Although only a few ways of fixing the placement and orientation insert 11 to the insertion shell 1 have been described explicitly, clearly any other alternative fixing method is included within the field of protection on the invention. For example, the placement and orientation insert 11 could be fixed to the peripheral receiving structure 8 of the insertion shell 1 by forcible insertion of the placement and orientation insert 11.

The insertion shell 1 can be of metal, titanium or a chromium and cobalt steel alloy. The insertion shell 1 can equally be of PEEK (polyetheretherketone) or any other appropriate material. The external convex face 2 of the insertion shell 1 can advantageously be covered with a layer of HAP (hydroxyapatite).

In practice, good anti-luxation capabilities and good resistance to deformation during impaction have been achieved with a ceramic fixed final joint insert 4 of thickness E' less than or equal to 3.5 mm engaged in a metal insertion shell 1 of thickness E less than or equal to 4 mm.

The present invention is not limited to the embodiments that have been explicitly described, but includes variants and generalizations thereof contained within the scope of the following claims.

The invention claimed is:

1. Ex-vivo cotyle assembly comprising:
   a metal insertion shell (1), having a substantially hemispherical convex exterior anchor face (2) conformed to be anchored in a cotyle cavity in the pelvis of a patient, and having a concave receiving face (3) with an annular edge (9),
   a ceramic fixed final joint insert (4), distinct from, and being manufactured separately from, the insertion shell (1), having an exterior face (5) ex-vivo engaged in the concave receiving face (3) of the insertion shell (1), and having an interior receiving face (6) including a substantially hemispherical concave joint surface (7) to enable the engagement and the pivoting of a femoral prosthesis head or of a mobile joint insert,
   the ceramic fixed final joint insert (4) having a thickness (E') less than or equal to approximately 4 mm,
   wherein:
   the insertion shell (1) has, in a vicinity of its annular edge (9), a thickness (E) less than or equal to approximately 4 mm and greater than 2 mm,
   the insertion shell (1) comprises a peripheral receiving structure (8) projecting beyond the receiving face (6) of the fixed final joint insert (4) inserted in the insertion shell (1) and including an annular receiving face (10), wherein the insertion shell (1) and the ceramic fixed final joint insert (4) each have conical surfaces, wherein said conical surfaces bear upon each other when the insert (4) is impacted against the insertion shell (1), and wherein a placement and orientation insert (11), including an assembly structure (12) to which the impacter (15) can be removably fixed, is removably fixed to the annular receiving face (10) of the insertion shell (1) in the presence of the ceramic fixed final joint insert (4), in order to enable an impaction of the ex-vivo assembly into the pelvis of a patient, providing a simultaneous impaction of the metal insertion shell (1) and of the ceramic fixed final joint insert (4) into the pelvis of the patient, and wherein the insertion shell (1), the ceramic fixed final joint insert (4) and the placement and orientation insert (11) are assembled and packaged in a microbial protection envelope in a sterile state, with the ceramic fixed final joint insert (4) engaged in the insertion shell (1), and with the placement and orientation insert (11) fixed to the insertion shell (1).

2. Cotyle assembly according to claim 1, wherein the annular receiving face (10) extends from and is continuous with the concave receiving face (3) of the insertion shell (1).

3. Cotyle assembly according to claim 1, wherein the placement and orientation insert (11) is made of polyethylene.

4. Cotyle assembly according to claim 1, wherein the assembly structure (12) comprises a threaded fixing hole (13) formed in the placement and orientation insert (11), enabling the screwing in of a corresponding threaded portion (14) of the impacter (15).

5. Cotyle assembly according to claim 4, wherein the threaded fixing hole (13) is an open hole.

6. Cotyle assembly according to claim 4, wherein:
the placement and orientation insert (11) is conformed so that there remains a free space (S) between the placement and orientation insert (11) and the bottom of the concave joint surface (7) of the fixed final joint insert (4) once the placement and orientation insert (11) is fixed to the peripheral receiving structure (8) of the insertion shell (1),
the placement and orientation insert (11) is in sealed contact at its periphery in the short annular extension (9) of the insertion shell (1),
the fixing hole (13) is an open hole, providing communication between the exterior and the free space (S) between the placement and orientation insert (11) and the fixed final joint insert (4), and sized to engage therein in sealed manner the end of a syringe.

7. Cotyle assembly according to claim 1, wherein the placement and orientation insert (11) fixed to the annular receiving face (10) of the insertion shell (1) bears on or is at a small distance (e) from the interior receiving face (6) of the ceramic fixed final joint insert (4).

8. Cotyle assembly according to claim 1, wherein the placement and orientation insert (11), fixed to the annular receiving face (10), includes one or more projecting elastic ribs (11a) adapted to come to bear on the ceramic fixed final joint insert (4) to retain it in the insertion shell (1).

9. Cotyle assembly according to claim 1, wherein:
the peripheral receiving structure (8) includes a continuous or discontinuous annular groove (16),
the placement and orientation insert (11) includes a continuous or discontinuous annular rib (17) elastically engaged in the annular groove (16).

10. Cotyle assembly according to claim 9, wherein:
the annular groove (16) is continuous,
the annular rib (17) of the placement and orientation insert (11) is a continuous exterior annular rib (17), elastically engaged in the annular groove (16).

11. Cotyle assembly according to claim 1, wherein:
the peripheral receiving structure (8) includes an internal or external thread,
the placement and orientation insert (11) includes an external or internal thread, cooperating with the thread of the peripheral receiving structure (8) to fix the placement and orientation insert removably by screwing it to the peripheral receiving structure (8).

12. Cotyle assembly according to claim 1, wherein the insertion shell (1) includes an external fixing lug (25).

13. Ex-vivo cotyle assembly comprising:
a metal insertion shell (1), having a substantially hemispherical convex exterior anchor face (2) conformed to be anchored in a cotyle cavity in the pelvis of a patient, and having a concave receiving face (3) with an annular edge (9),
a ceramic fixed final joint insert (4), distinct from, and being manufactured separately from, the insertion shell (1), having an exterior face (5) ex-vivo engaged in the concave receiving face (3) of the insertion shell (1), and having an interior receiving face (6) including a substantially hemispherical concave joint surface (7) to enable the engagement and the pivoting of a femoral prosthesis head or of a mobile joint insert,
wherein the insertion shell (1) and the ceramic fixed final joint insert (4) each have conical surfaces, and wherein said conical surfaces bear upon each other when the insert (4) is impacted against the insertion shell (1),
wherein the insertion shell (1) comprises a peripheral receiving structure (8) projecting beyond the receiving face (6) of the fixed final joint insert (4) inserted in the insertion shell (1) and including an annular receiving face (10),
and wherein a placement an orientation insert (11), including an assembly structure (12) to which an impacter (15) can be removably fixed, is removably fixed to the annular receiving face (10), in order to enable an impaction of the ex-vivo assembly into the pelvis of a patient, providing a simultaneous impaction of the metal insertion shell (1) and of the ceramic fixed final joint insert (4) into the pelvis of the patient,
and wherein the insertion shell (1), the ceramic fixed final joint insert (4) and the placement and orientation insert (11) are assembled and packaged in, a microbial protection envelope in a sterile state, with the ceramic fixed final joint insert (4) engaged in the insertion shell (1), and with the placement and orientation insert (11) fixed to the insertion shell (1).

14. Ex-vivo cotyle assembly comprising:
a metal insertion shell (1), having a substantially hemispherical convex exterior anchor face (2) conformed to be anchored in a cotyle cavity in the pelvis of a patient, and having a concave receiving face (3) with an annular edge (9),
a ceramic fixed final joint insert (4), distinct from and being manufactured separately from the insertion shell (1), having an exterior face (5) ex-vivo engaged in the concave receiving face (3) of the insertion shell (1), and having an interior receiving face (6) including a substantially hemispherical concave joint surface (7) to enable the engagement and the pivoting of a femoral prosthesis head or of a mobile joint insert, wherein:

the insertion shell (1) and the ceramic fixed final joint insert (4) each have conical surfaces, said conical surfaces bear upon each other when the insert (4) is impacted against the insertion shell (1), the insertion shell (1) comprises a peripheral receiving structure (8), a placement and orientation insert (11), including an assembly structure (12) to which an impacter (15) can be removably fixed, is removably fixed to the peripheral receiving structure (8) of the insertion shell (1), in order to enable an impaction of the ex-vivo assembly into the pelvis of a patient, providing a simultaneous impaction of the metal insertion shell (1) and of the ceramic fixed final joint insert (4) into the pelvis of the patient, the placement and orientation insert (11) fixed to the peripheral receiving structure (8) of the insertion shell (1) bears on the ceramic fixed final joint insert (4).

\* \* \* \* \*